(12) United States Patent
Paul

(10) Patent No.: US 10,092,332 B2
(45) Date of Patent: *Oct. 9, 2018

(54) INTRAMEDULLARY NAILS

(71) Applicant: GLOBUS MEDICAL, INC., Audubon, PA (US)

(72) Inventor: David C. Paul, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/462,045

(22) Filed: Mar. 17, 2017

(65) Prior Publication Data

US 2017/0181777 A1 Jun. 29, 2017

Related U.S. Application Data

(63) Continuation of application No. 14/161,200, filed on Jan. 22, 2014, now Pat. No. 9,629,670.

(51) Int. Cl.
*A61B 17/72* (2006.01)

(52) U.S. Cl.
CPC ...... *A61B 17/7266* (2013.01); *A61B 17/7225* (2013.01); *A61B 17/7233* (2013.01)

(58) Field of Classification Search
CPC ............ A61B 17/7266; A61B 17/7216; A61B 17/7225; A61B 17/7233; A61B 17/7258
USPC .............................................. 606/62, 63, 68
See application file for complete search history.

(56) References Cited

U.S. PATENT DOCUMENTS

| | | | | |
|---|---|---|---|---|
| 4,237,875 A | * | 12/1980 | Termanini | A61B 17/7225 606/63 |
| 4,261,351 A | * | 4/1981 | Scherfel | A61B 17/72 606/62 |
| 4,453,539 A | * | 6/1984 | Raftopoulos | A61B 17/7258 606/63 |
| 4,590,930 A | * | 5/1986 | Kurth | A61B 17/7258 606/63 |
| 5,179,915 A | * | 1/1993 | Cohen | A61B 17/1717 606/62 |
| 5,704,938 A | * | 1/1998 | Staehlin | A61B 17/7216 606/105 |
| 5,961,553 A | * | 10/1999 | Coty | A61B 17/7216 606/62 |
| 7,753,915 B1 | * | 7/2010 | Eksler | A61B 17/663 606/105 |
| 8,162,942 B2 | * | 4/2012 | Coati | A61B 17/7266 606/63 |
| 9,629,670 B2 | * | 4/2017 | Paul | A61B 17/7266 |
| 2005/0246034 A1 | * | 11/2005 | Soubeiran | A61B 17/7216 623/23.45 |
| 2011/0224670 A1 | * | 9/2011 | Bolar | A61B 17/7266 606/62 |

* cited by examiner

*Primary Examiner* — Pedro Philogene
*Assistant Examiner* — David C Comstock

(57) ABSTRACT

The present invention is generally directed to intramedullary nails that can include a keel configured for rotational stabilization and/or a multi-sectioned rod configured to apply compression to a fracture.

20 Claims, 4 Drawing Sheets

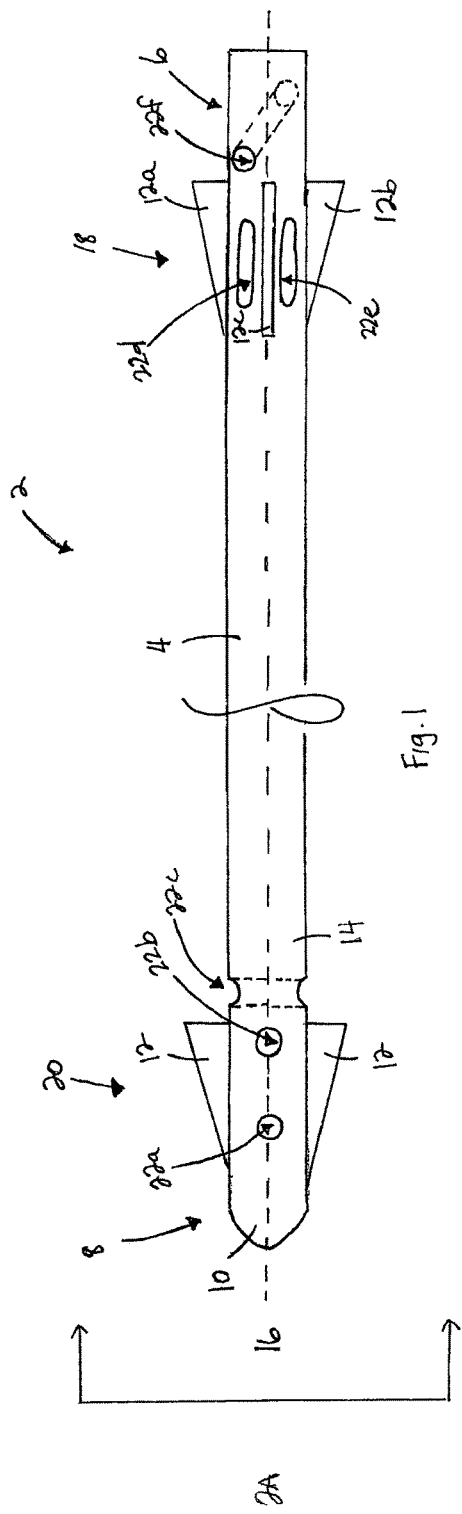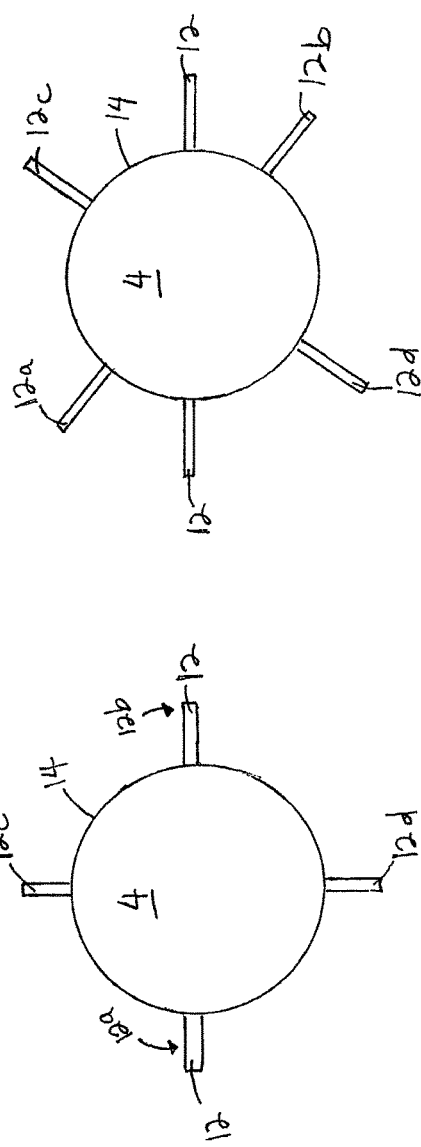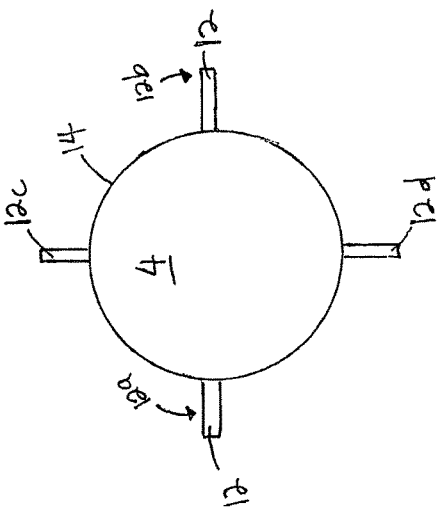

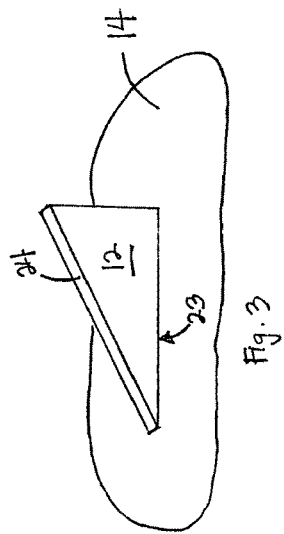
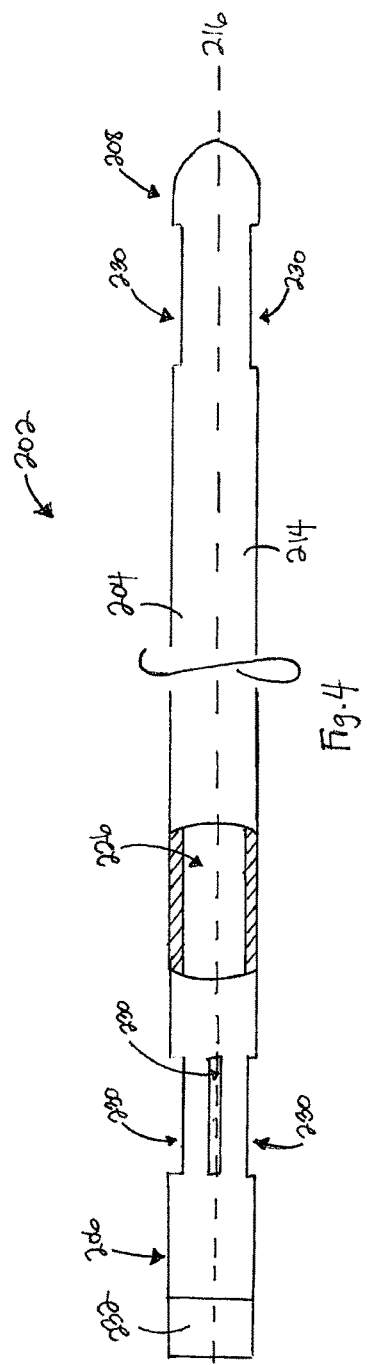
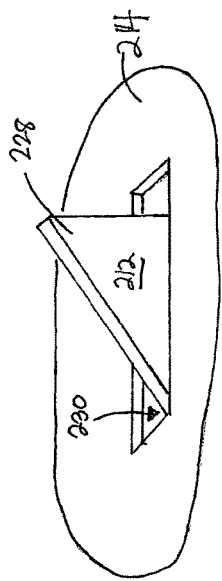
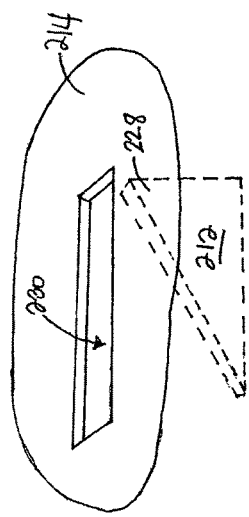

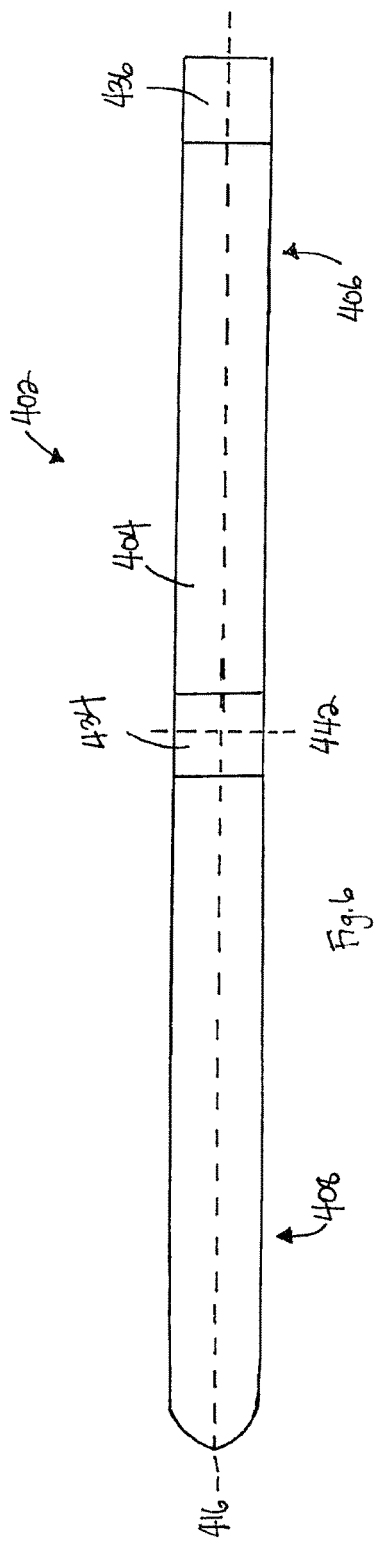
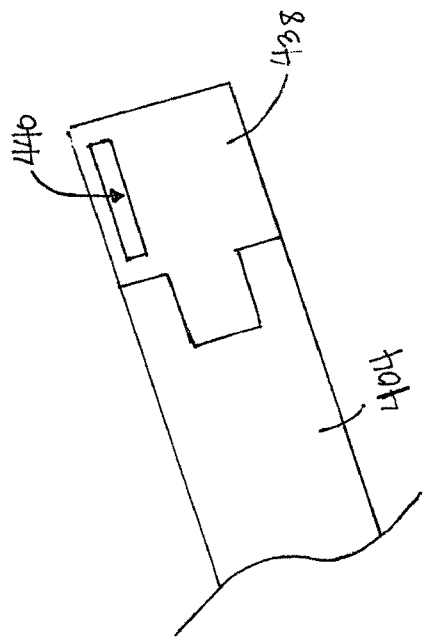
Fig. 7

INTRAMEDULLARY NAILS

CROSS-REFERENCE TO RELATED APPLICATIONS

This application is a continuation of U.S. patent application Ser. No. 14/161,200, filed on Jan. 22, 2012, which is incorporated herein by reference.

FIELD OF THE INVENTION

The present invention relates to intramedullary nails and methods of installation thereof.

BACKGROUND OF THE INVENTION

Traumatic injuries to the skeletal system can be treated in a variety of ways. In general, treatments may include reducing or restoring any displaced bone fragments into proper alignment, and immobilizing the bones so that they can heal. Some fractures can be treated non-invasively, such as through the use of a cast or splint; other fractures may require a surgically-applied stabilization device.

Surgical devices used to stabilize broken bones can include, for example, plates, pins, screws, nails, and/or some combination thereof. When the bone that is fractured or broken is a long bone, such as the femur, tibia, fibula, humerus, radius, and ulna, an intramedullary nail may be used for treatment. An intramedullary nail can include a rod that is placed in the medullary canal of a broken bone and secured to the proximal and distal ends of the bone with locking screws. In use, an intramedullary nail can help to immobilize a broken bone while also reducing the weight or load being placed on the bone.

SUMMARY OF THE INVENTION

One drawback of current intramedullary nails is that the insertion and locking of the nail may occur in two separate steps, as the rod is first inserted into the medullary canal and subsequently fixed in place by the locking screws. Since the rod is not fixed in place upon insertion, it may rotate undesirably within the medullary canal. Additionally, a multi-step process can require a significant amount of time. Another drawback of current intramedullary nails is that reduction and/or compression of the bone fragments may take place separately from rod installation. Some compression techniques may also involve the use of additional screws, which can result in added trauma to the surrounding area. Furthermore, a multi-step process can require a significant amount of time, and multiple components can increase the complexity of the procedure. Accordingly, there exists a need for new and improved intramedullary nails.

Some embodiments herein are directed to an intramedullary nail that can include a rod comprising a proximal portion and a distal portion, and at least one elongate keel disposed longitudinally on an outer surface of the rod.

Other embodiments are directed to a method of installing an intramedullary nail that can include providing an intramedullary nail comprising a rod having a proximal portion, a distal portion, and at least one elongate keel disposed longitudinally on an outer surface of the rod; cutting at least one groove within a medullary canal, wherein the groove is configured to receive the elongate keel; and inserting the intramedullary nail into the medullary canal such that the elongate keel is received in the groove.

Some embodiments herein are directed to an intramedullary nail that can include a rod comprising a proximal portion, a distal portion, and an outer surface; and a deployable keel oriented longitudinally along the rod; wherein the deployable keel is configured to transition from a retracted position to a deployed position.

Other embodiments are directed to a method of installing an intramedullary nail that can include providing an intramedullary nail comprising a rod having a proximal portion, and a distal portion, at least one deployable keel oriented longitudinally along the rod and in a retracted position; cutting at least one groove within a medullary canal, wherein the groove is configured to receive at least a portion of the deployable keel; inserting the intramedullary nail into the medullary canal; and deploying the deployable keel to transition from the retracted position to a deployed position, such that the deployable keel is received in the groove.

Some embodiments herein are directed to an intramedullary nail that can include a rod comprising a proximal portion and a distal portion and configured to transition from an expanded configuration to a compressed configuration; a compression mechanism configured to move the proximal and distal portions axially with respect to one another from the expanded configuration to the compressed configuration; and an actuator assembly configured to actuate the compression mechanism and comprising an actuator located on the proximal portion of the rod.

Other embodiments are directed to a method of installing an intramedullary nail that can include providing an intramedullary nail comprising a rod comprising a proximal portion and a distal portion and configured to transition from an expanded configuration to a compressed configuration, a compression mechanism configured to move the proximal and distal portions axially with respect to one another, and an actuator assembly configured to actuate the compression mechanism and comprising an actuator located on the proximal portion of the rod; inserting the intramedullary nail in the expanded configuration into a medullary canal of a fractured bone, the fractured bone comprising a first bone fragment and a second bone fragment separated by a first distance; securing the distal portion to the first bone fragment; and actuating the compression mechanism to transition the rod from the expanded configuration to the compressed configuration, such that the distal portion and the first bone fragment are moved axially to a second position wherein the first and second bone fragments are separated by a second distance that is less than the first distance.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a side view of an embodiment of an intramedullary nail disclosed herein;

FIGS. 2A-B illustrate variations on front views of an intramedullary nail disclosed herein;

FIG. 3 is a detail view of an elongate keel disclosed herein;

FIG. 4 is a side view, in partial cross-section, of an embodiment of an intramedullary nail disclosed herein;

FIG. 5A is a detail view of one embodiment of a deployable keel in a retracted position;

FIG. 5B is a detail view of one embodiment of a deployable keel in a deployed position;

FIG. 6 is a schematic view of an embodiment of an intramedullary nail including a compression mechanism disclosed herein; and FIG. 7 is a schematic side view of one embodiment of a proximal end of an intramedullary nail including a compression mechanism disclosed herein.

DETAILED DESCRIPTION OF THE EMBODIMENTS

Figure 8:
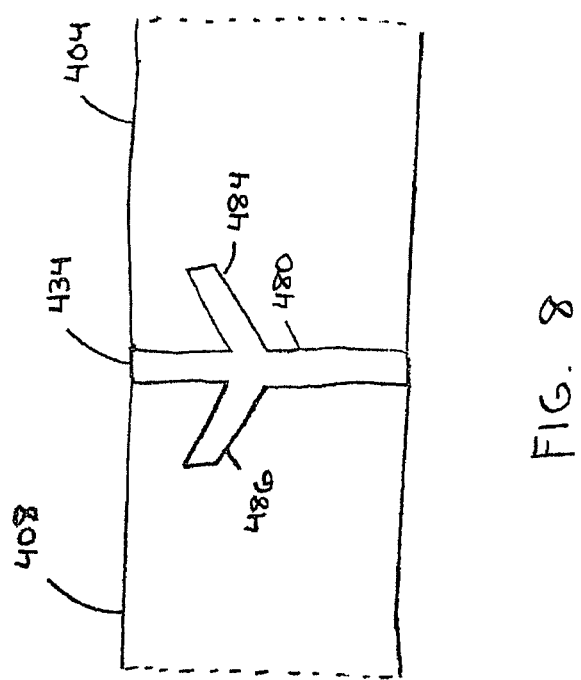
FIG. 8 is a cross-sectional view of one embodiment of an intramedullary nail including a compression mechanism including ramps.

Embodiments herein are generally directed to intramedullary nails that can include a fixation feature and/or a compression element. In embodiments that include a fixation feature, a separate locking screw may not be needed. Accordingly, these intramedullary nails may be configured for insertion and locking in a single step. Furthermore, even if used in combination with a separate locking screw, these intramedullary nails can provide more stable placement as compared to other intramedullary nails that do not include a fixation feature. Compression of bone fragments, for example, through the application of compression plates, has been used to promote healing by pushing or pulling the fragments together, thereby reducing the gap that must be filled by new bone growth. Embodiments herein that include a compression element may thus advantageously combine the benefits of an intramedullary nail with the benefits of axial compression. Furthermore, although these features may be discussed separately herein, it should be appreciated that intramedullary nails that include any combination of these features are within the scope of the present disclosure.

Turning to FIG. 1, some embodiments herein are directed to an intramedullary nail 2 that can include a rod 4 having a proximal portion 6 and a distal portion 8. The rod 4 can be sized and configured to fit within a medullary canal of a long bone, such as a femur, tibia, fibula, humerus, radius, and/or ulna. For example, when configured for placement within a femur, the rod 4 can have a length, extending from a proximal end to a distal end, in the range of from about 30 cm to about 50 cm, and a diameter in the range of from about 0.5 cm to about 2 cm. As another example, when configured for placement within a humerus, the rod 4 can have a length, extending from a proximal end to a distal end, in the range of from about 15 cm to about 35 cm, and a diameter in the range of from about 0.5 cm to about 1.5 cm. It can be manufactured according to techniques known in the art and can be machined from any suitable materials, including metals such as titanium, titanium alloys, and stainless steel. In some embodiments, the rod can be straight; in other embodiments, the rod can be curved to conform to the shape of the medullary canal and/or other anatomical feature. The rod 4 can have a generally round cross section with either a constant or variable outer diameter. The rod 4 can include a longitudinal axis 16 that extends from a proximal end to a distal end. In some embodiments, the rod can be solid. In other embodiments, the rod can be hollow. For example, the rod can include a lumen extending longitudinally therethrough. The lumen can have a constant or variable diameter. The distal end of the rod 4 can include a distal tip 10. In some embodiments, the distal tip 10 can be tapered to facilitate insertion of the rod into the medullary canal.

The intramedullary nail 2 can further include at least one fixation feature, such as an elongate keel 12. The elongate keel 12 can act as an anti-rotation mechanism, e.g., it can advantageously inhibit or reduce rotation of the intramedullary nail 2 within the medullary canal. The elongate keel 12 can be disposed longitudinally on an outer surface 14 of the rod 4. For example, the base 23 of elongate keel 12, illustrated in FIG. 3, can extend parallel to the longitudinal axis 16 of the rod 4. In some embodiments, the intramedullary nail 2 can include a plurality of elongate keels. The elongate keels can be distributed anywhere along the outer surface 14 of the rod 4 with respect to its length and/or circumference. As illustrated in FIG. 1, the proximal portion 6 and the distal portion 8 can each include a plurality of elongate keels. In some embodiments, the elongate keels can be staggered along the length of the rod 4. In other embodiments, the rod 4 can include a first row 18 of elongate keels situated at the same longitudinal position along the rod 4, as illustrated in FIG. 1 with respect to elongate keels 12a and 12b. It is noted that specifically identified elongate keels 12a-d as discussed herein can include any and all of the same features disclosed in general with respect to elongate keel 12. In some embodiments, the rod 4 can include two or more rows of elongate keels distributed thereon. For example, the rod 4 can include a first row of keels on the proximal portion 6 and a second row 20 of keels on the distal portion 8. The elongate keels can be disposed anywhere around the circumference of the rod. As illustrated in FIG. 2A, the first and second rows of keels 18, 20 can be aligned around the circumference the rod 4. In other embodiments, such as that illustrated in FIG. 2B, the first and second rows of keels 18, 20 can be staggered around the circumference of the rod 4. As further illustrated in FIGS. 2A-B, the elongate keels can generally extend orthogonally from the outer surface 14 of the rod 4. In other embodiments, one or more elongate keels may extend from the outer surface 14 of the rod 4 at another angle between 0° and 180°.

Turning to FIG. 3, the details of one example of an elongate keel 12 are illustrated. The elongate keel 12 can include a base 23 and an edge 24. The elongate keel 12 can be attached to the outer surface 14 of the rod 4 at the base 23. For example, the base 23 can be welded to the rod 4. In another example, the elongate keel 12 and the rod 4 can be machined in a single piece. In some embodiments, the edge 24 can be blunt, as illustrated in FIG. 3. In other embodiments, the edge 24 can be sharpened (e.g., can include a blade). In yet other embodiments, the edge 24 can be rounded. The edge 24 can be straight from a distal to proximal end, as illustrated in FIG. 3, or it can be curved. The elongate keel 12 can have a height as measured from the base 23 to the edge 24 and a length as defined by the base 23. In some embodiments, the elongate keel 12 can have a uniform height (e.g., can have a generally rectangular profile). In other embodiments, the elongate keel 12 can have a variable height. For example, the elongate keel 12 can have a height that increases in the proximal direction (e.g., can have a generally triangular profile). As another example, the elongate keel 12 can have a profile in the shape of a right triangle, an obtuse triangle, or an acute triangle. The length of the elongate keel 12 can vary. In some embodiments, the length can be in the range of from about 5% to about 30% of the length of the rod 4. In other embodiments, the length of the elongate keel 12 can be equal to at least about 10% of the length of the rod 4.

Returning to FIG. 1, in some embodiments, the rod 4 can include one or more screw holes. As discussed herein, some of the present embodiments can include an anti-rotation mechanism, such as elongate keel 12. Advantageously, these embodiments may be configured for insertion into the medullary canal and locking therein in a single step. Consequently, separate locking screws may advantageously not be required. Regardless, in some embodiments, such as that shown in FIG. 1, the rod 4 may optionally include one or more screw holes 22a-f configured to receive one or more locking screws (not shown). In these embodiments, the screw holes and corresponding locking screws can provide supplemental stability. As illustrated in FIG. 1, the screw holes can be distributed around the circumference of the rod. The screw holes can also be distributed along the proximal and/or distal portions of the rod. In some embodiments, the rod can include a plurality of screw holes 22d-f in the proximal portion and a plurality of screw holes 22a-c in the distal portion.

Each screw hole can define a channel that passes through the rod, optionally intersecting its longitudinal axis 16. The channels can intersect the longitudinal axis at any angle. For example, in some embodiments a rod can include a channel that is perpendicular to the longitudinal axis 16, such as those defined by screw holes 22a-c. In other embodiments, a rod can include a channel that intersects the longitudinal axis at an approximately 45° angle, such as that defined by screw hole 22f. The channels can also be distributed along the rod at various angles relative to each other. For example, in some embodiments, a first channel and a second channel can pass through the rod at approximately 90° relative to each other, such as those defined by screw holes 22b and 22c, respectively. In other embodiments, a first channel and a second channel can be aligned (e.g., 0° relative to each other), such as those defined by screw holes 22a and 22b. In yet other embodiments, the first and second channels can be staggered by any angle in the range of 0° to 90°.

The screw holes can be of varying shapes and cross-sections. In some embodiments, they can be circular, as illustrated in FIG. 1 with respect to screw holes 22a-c and 22f. In other embodiments, they can be ovular (e.g., slots), as illustrated with respect to screw holes 22d-e. In some embodiments, the screw holes can have a constant diameter (e.g., rectangular cross-section). In other embodiments, the screw holes can have a tapered diameter (e.g., trapezoidal cross-section). When screws are inserted eccentrically, these screw holes can advantageously act as compression slots and can be configured to apply compression to the fracture. These compression slots can be used alone or in conjunction with the compression mechanisms described herein. Various locking screws can be received in the screw holes 22a-f, including but not limited to cortical screws and cancellous screws, as well as fully- and partially-threaded versions thereof.

Embodiments herein are also directed to methods of installing the intramedullary nail 2. These methods can include providing the intramedullary nail 2 and cutting at least one groove within a medullary canal (e.g., on an interior surface of a long bone). The groove can be sized and configured to receive the elongate keel 12 at least partially therein. For example, the groove can have a depth in the range of from about 1 mm to about 3 mm. Any cutter known in the art can be used. Subsequently, the intramedullary nail 2 can be inserted into the medullary canal such that at least a portion of the elongate keel 12 (e.g., edge 24) is received in the groove. Advantageously, the groove can act as a track, with the elongate keel 12 sliding therein. The elongate keel and groove can thus be used to guide the intramedullary nail 2 into the medullary canal. Additionally, the elongate keel 12 can prevent or minimize rotation of the intramedullary nail 2 within the medullary canal.

Methods herein can also include other steps utilized in the art for the installation of intramedullary nails. For example, some embodiments herein can optionally include preparing the medullary canal prior to cutting the groove therein. The preparation step can include, for example, reduction of a fractured bone within which the medullary canal is situated and/or defining a passageway through the medullary canal (e.g., through the use of a drill, awl, and/or reamer). Optionally, methods herein can also include inserting a locking screw into a screw hole in the intramedullary nail 2. However, as discussed herein, this step may not be required, as the elongate keels 12 can provide sufficient rotational stability such that additional locking mechanisms are not needed.

Some embodiments herein are directed to an intramedullary nail that can include a rod and a deployable keel. One example is intramedullary nail 202, illustrated in FIGS. 4-5B. In some embodiments, the intramedullary nail 202 can include a rod 204 having a lumen 226 extending therethrough, e.g., between a proximal end 206 and a distal end 208. In some embodiments, the rod 204 can also include an opening 230. The opening 230 can be configured to receive at least a portion of the deployable keel 212. For example, the opening 230 can be rectangular or slot-shaped. As illustrated in FIG. 4, the rod 204 can include a plurality of openings 230 (e.g., 2, 3, 4, 5, 6, or more). The number of openings 230 can be equal to the number of deployable keels 212 present on the intramedullary nail 202. In some embodiments, a proximal cap 232 can also be connected to the proximal end 206 of the rod 204. The rod 204 can also include other features described herein with respect to rod 4 of intramedullary nail 2.

The intramedullary nail 202 can also include a deployable keel 212. The deployable keel 212 can be oriented longitudinally along the rod 204, and can be configured to transition from a retracted position to a deployed position. In some embodiments, the transition is reversible (e.g., the deployable keel 212 can transition between the retracted and deployed positions). FIGS. 5A-B illustrate examples of deployable keel 212 in the retracted and deployed positions, respectively. When in the deployed position, the deployable keel 212 can extend away from the rod. In some embodiments, the deployable keel 212 can include a tip 228 (e.g., the tallest point on the deployable keel 212). When the deployable keel 212 is in the deployed position, the tip 228 can be farther away from an outer surface 214 of the rod 204 as compared to when the deployable keel 212 is in the retracted position. As illustrated in FIGS. 5A-B, the deployable keel 212 can pass through the opening 230 of the rod 204 when transitioning from the retracted position to the deployed position. In some embodiments, when in the retracted position, at least a portion of the deployable keel 212 can be within the lumen 226 of the rod 204, and, when in the deployed position, at least a portion of the deployable keel 212 can be outside of the lumen 226. In some embodiments, at least a portion of the deployable keel 212 can be compressed within the lumen 226 when in the retracted position. The deployable keel 212 can also include other features described herein with respect to elongate keel 12 of intramedullary nail 2.

In some embodiments, the intramedullary nail 202 can further include a deployment mechanism. The deployment mechanism can be configured to actuate the transition of the deployable keel 212 from the retracted position to the deployed position. The deployment mechanism can employ various components to deploy the deployable keel 212. For example, the deployment mechanism can include a shaft that is disposed within the lumen 226, and to which the deployable keel 212 is operatively connected (e.g., through a hinge or other linkage). In some embodiments, the shaft can be configured for linear motion relative to longitudinal axis 216, such that the deployable keel 212 can slide in a proximal-distal direction from the retracted to the deployed position. In other embodiments, the shaft can be configured for rotational motion relative to the longitudinal axis 216, such that the deployable keel 212 can rotate in a clockwise or counter-clockwise direction from the retracted to the deployed position. In yet other embodiments, the shaft may include another component, such as a sliding ring, that can be configured for linear and/or rotational movement. In some embodiments, the deployment mechanism can additionally include one or more springs and/or other tension or compression members that can apply force to the shaft and/or deployable keel 212.

Although the components of the deployment mechanism may be distributed throughout the intramedullary nail 202, at least a portion of the deployment mechanism may be disposed at the proximal portion 206 of the rod 204. For example, an actuator can be located in or adjacent to the proximal cap 232. In some embodiments, the proximal cap 232 can include one or more of a button, switch, knob, threaded nut, and lever which is configured to actuate the deployment mechanism.

In use, a method of installing the intramedullary nail 202 can include providing the intramedullary nail 202, wherein the deployable keel 212 is in the retracted position. Optionally, the method can include cutting a groove within a medullary canal as described herein. The groove can be configured to receive at least a portion of the deployable keel 212. Subsequently, the intramedullary nail 202 can be inserted into the medullary canal, and the deployable keel can be deployed from the retracted position to the deployed position. If a groove is present, the groove can receive the deployable keel when in the deployed position. In embodiments where the intramedullary nail 202 includes a deployment mechanism, the deployable keel can be deployed by actuating the deployment mechanism. For example, the deployable keel can be deployed by pushing a button, sliding a switch, turning a knob, threading a nut, and/or pulling a lever located on or in the proximal cap 232. Advantageously, once the keel is deployed, the intramedullary nail 202 may be locked and/or stabilized within the medullary canal. Other steps practiced in the art with respect to installation of intramedullary nails may also be used, as discussed herein. For example, additional locking elements such as screws, although not required, may optionally be utilized to provide supplemental stability.

Other embodiments herein are directed to an intramedullary nail that can include a compression element. As illustrated in FIG. 6, intramedullary nail 402 can include a rod 404, a compression mechanism 434, and an actuator 436. The rod 404 can include a proximal portion 406, a distal portion 408, and a longitudinal axis 416. Although the proximal and distal portions 406, 408 are illustrated in FIG. 6 as being of approximately equal length, those skilled in the art may appreciate that in other embodiments, the proximal and distal portions 406, 408 may be of unequal length. The rod can be configured to transition from an expanded configuration having a first length to a compressed configuration having a second length, wherein the second length is less than the first length. For example, the rod can be shorter in the compressed configuration and longer in the expanded configuration. The proximal portion 406 and/or the distal portion 408 can be configured to move axially with respect to one another, resulting in expansion and/or compression of the intramedullary nail 402. For example, the distal portion 408 can be configured to slide along longitudinal axis 416 towards and/or away from the proximal portion 406. Conversely, the proximal portion 406 can be configured to slide along longitudinal axis 416 towards and/or away from the distal portion 408. The proximal and/or distal portions 406, 408 can include a lumen extending longitudinally therethrough. In some embodiments, at least a portion of the proximal portion 406 can be configured to be received within the lumen of distal portion 408, or vice versa. The rod 404 can also include other features described herein with respect to the rods of intramedullary nail 2 and/or intramedullary nail 202, such as elongate and/or deployable keels.

The compression mechanism 434 can be configured to move the proximal and distal portions 406, 408 axially with respect to one another. Various mechanics that effect linear expansion and/or compression can be used as part of the compression mechanism 434. In some embodiments, the compression mechanism 434 can include a compression member, wherein rotation of the compression member results in axial translation of the proximal and/or distal portions 406, 408. The compression member can be disposed between, around, and/or within the proximal and/or distal portions 406, 408. For example, in one embodiment, the compression mechanism 434 can include a compression member, such as an internally-threaded sleeve, rotatably attached around the proximal portion 406 of the rod 404 and configured to mate with external threading on the distal portion 408 of the rod 404. In use, when the sleeve is rotated in one direction, it can threadably engage the distal portion 408 and cause the distal portion to slide axially, e.g., in a proximal direction towards proximal portion 406. In some embodiments, the distal portion 408 can be received within a lumen of the proximal portion 406. When the sleeve is rotated in the opposite direction, it can cause the distal portion 408 to slide in the opposite direction away from proximal portion 406. Those skilled in the art may appreciate that in other embodiments, the internally-threaded sleeve can be rotatably attached to the distal portion 408 of rod 404 and configured to mate with external threading on the proximal portion 408 of the rod.

In some embodiments, the internally-threaded sleeve can be a gear member. The gear member can include a plurality of teeth extending around a periphery of the gear and configured to engage an actuator, such as a tool having a bevel gear. In use, when the tool having a bevel gear engages the teeth and rotates about the axis of the bevel gear, it can cause the gear member to rotate in a perpendicular direction. As the gear member rotates, its internal threading can engage the external threading on the distal portion 408 of the rod 404, causing the distal portion 408 to translate axially.

In other embodiments, the compression member can be disposed within the proximal and/or distal portions 406, 408. In these embodiments, the compression member can include, for example, a central gear or cam. In yet other embodiments, the compression member can be disposed between the proximal and/or distal portions 406, 408. In these embodiments, the compression member can include, for example, a scissor jack or a tapered screw.

The compression mechanism can optionally include one or more additional features. For example, some embodiments can include a locking member. The locking member can selectively inhibit rotation of the compression member, thereby locking the rod 404 at a particular length. Other embodiments can include a stabilization assembly. For example, the proximal portion 406 can include a pin configured to ride in a longitudinal slot disposed on the externally-threaded section of the distal portion 408. In these embodiments, the pin and slot can prevent rotational movement of the proximal and distal portions 406, 408. The ends of the slot can also define the maximum allowable distance of translational motion for the distal portion 408.

In some embodiments, the compression mechanism 434 can include a compression member configured for linear movement. Linear movement of the compression member (e.g., along a transverse axis 442 of the rod 404) can result in linear movement of the proximal and/or distal portions 406, 408 in a perpendicular direction (e.g., along the longitudinal axis 416). For example, in one embodiment, the compression mechanism 434 can include a body portion and a translation member (shown in FIG. 8). The body portion can be configured to be received between the proximal and distal portions 406, 408 of the rod 404. As shown in FIG. 8, the translation member 480, which may act as the compression member, can be configured to be received within the body portion and can include a first angled surface 484 and a second angled surface 486.

In some embodiments, the first and second angled surfaces 484, 486 of the translation member can be configured to engage the proximal and distal portions 406, 408 of the rod 404. In some embodiments, the proximal and distal portions 406, 408 can include angled slots, grooves, and/or ramps that correspond to the angled surfaces on the translation member, and that can be configured to receive a portion of the translation member therein. In other embodiments, the proximal and distal portions 406, 408 can be connected to separate inserts having angled slots, grooves, and/or ramps that can engage the translation member. Movement of the translation member along transverse axis 442 can cause the first angled surface to push against the proximal portion 406 and the second angled surface to push against the distal portion 408, resulting in compression of the rod 404 (e.g., proximal and distal portions 406, 408 moving towards from each other). In some embodiments, movement of the translation member in the opposite direction along transverse axis 442 can result in expansion of the rod 404 (e.g., proximal and distal portions 406, 408 moving away from each other). FIG. 8 illustrates a compression mechanism 434 (e.g., including the translation member 480) in a fully contracted or compressed state, rather than in an expanded state.

In other embodiments, the body portion can include a proximal end and a distal end, each of which can include one or more angled slots, grooves, and/or ramps. The angled slots, grooves, and/or ramps can be configured to receive a protuberance extending from each of the proximal and distal portions 406, 408. In use, translation of the translation member along transverse axis 442 can engage the proximal and distal portions 406, 408, causing the protuberances to slide along the angled slots, grooves, and/or ramps of the body portion, resulting in compression of the rod 404 along longitudinal axis 416. Translation of the translation member in the opposite direction along transverse axis 442 can cause the protuberances to also slide in an opposite direction along the angled slots, grooves, and/or ramps of the body portion, resulting in expansion of the rod 404 along longitudinal axis 416.

As illustrated in FIG. 6, the actuator assembly can include an actuator 436 located on the proximal portion 406 of the rod 408. For example, the actuator 436 can be located in a proximal cap. The actuator assembly can be configured to actuate the compression mechanism 434. For example, the actuator assembly can include, for example, a bevel gear, driver, wrench, ratchet, or other torque applicator that is operatively connected to the actuator 436 using mechanics known in the art. In some embodiments, the actuator 436 can be selected from a button, switch, knob, threaded nut, and lever.

As illustrated in FIG. 6, compression mechanism 434 can be disposed between the proximal and distal portions 406, 408 of the rod 404. However, in other embodiments, the compression mechanism can be located at the proximal end of the rod 404. For example, both the compression mechanism and the actuator can be located in a proximal cap 438, illustrated in FIG. 7. In some of these embodiments, a portion of the rod 404 can be received within the proximal cap 438 as part of the compression process. The proximal cap 438 can be situated at the proximal-most end of the rod 404. In some embodiments, the proximal cap 438 can further include a compression slot 440, which can be configured to facilitate translational movement of the rod 404 towards the proximal cap 438. In some embodiments, the compression cap can serve as an actuator to actuate the compression mechanism 434 located at the junction between the proximal portion 406 and distal portion 408 of the rod 404.

While the previous embodiments disclosed expansion and contraction of an intramedullary nail in an axial direction, in some embodiments, an intramedullary nail can be expanded in a radial direction. Any of the mechanisms discussed above, such as the use of ramped surfaces (shown in FIG. 8), can be used to expand an intramedullary nail in a radial direction. Advantageously, by expanding the intramedullary nail in a radial direction, this allows the intramedullary nail to increase a greater volume in the intramedullary canal, thereby reducing the likelihood of undesired rotation or movement of the nail within the canal. In some embodiments, radial expansion of the intramedullary nail in a radial direction results in a shortening of the length of the intramedullary nail, while in other embodiments, the length of the intramedullary nail can be kept substantially or completely constant during radial expansion.

In some embodiments, the intramedullary nail is capable of either axial or radial expansion/compression. In other embodiments, the intramedullary nail is capable of both axial and radial expansion/compression. The axial expansion/compression can be independent from the radial expansion/compression. In some embodiments, a first mechanism can control the axial expansion/compression, while a second mechanism can control the radial expansion/compression. In some embodiments, the mechanism for axial expansion/compression can be the same as the mechanism for radial expansion/compression, while in other embodiments, the mechanisms can be different. For example, axial changes can be made via a ramping mechanism, while radial changes can be made via a gear expansion mechanism.

Some embodiments herein are directed to a method of installing the intramedullary nail 402. Optionally, the medullary canal may be prepared prior to installation of the intramedullary nail, as described herein with respect to other embodiments. Methods of installing intramedullary nail 402 can include providing the intramedullary nail 402 and inserting it, in the expanded configuration, into a medullary canal of a fractured bone. The fractured bone can include a first bone fragment and a second bone fragment separated by a first distance. The distal portion 408 of the rod 404 can then be secured to the first bone fragment, e.g., via keels and/or locking screws as described herein. Subsequently, the compression mechanism 434 can be actuated, thereby transitioning the rod from the expanded configuration to the compressed configuration. The compression mechanism can be activated by actuating the actuator 436. For example, the rod 404 can be compressed by pushing a button, sliding a switch, turning a knob, threading a nut, and/or pulling a lever located on or in the proximal cap 438. The distal portion 408 and the first bone fragment can thereby be moved axially (e.g., proximally) to a second position. In the second, compressed position, the first and second bone fragments can be compressed such that they are separated by a second distance that is less than the first distance. In some embodiments, the intramedullary nail 402 can then be secured to the second bone fragment, e.g., via keels and/or locking screws. As discussed herein, the compression of the bone fragments can advantageously promote healing of the fracture and/or reduce recovery time.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A method of installing an intramedullary nail comprising:
   cutting a groove in a medullary canal of a bone;
   providing an intramedullary nail, the nail comprising:
      a rod comprising a proximal portion and a distal portion; and
      at least one elongate keel disposed longitudinally on an outer surface of the rod,
   wherein at least a portion of the keel is received within the groove such that the groove is capable of serving as a track for the keel to guide the intramedullary nail in the intramedullary canal; and
   deploying the intramedullary nail such that the intramedullary nail mechanically expands or retracts axially when the intramedullary nail is positioned in the medullary canal.

2. The method of claim 1, wherein the proximal portion and the distal portion of the rod each comprise a plurality of elongate keels.

3. The method of claim 1, wherein the elongate keel has a height that increases proximally.

4. The method of claim 1, wherein the elongate keel extends orthogonally from a surface of the rod.

5. The method of claim 1, wherein the elongate keel has a length that is equal to at least 10% of a length of the rod.

6. The method of claim 1, wherein the groove has a depth of generally about 1 mm to about 3 mm.

7. A method of installing an intramedullary nail comprising:
   cutting a groove in a medullary canal of a bone;
   providing an intramedullary nail, the nail comprising:
      a rod comprising a proximal portion, a distal portion, and an outer surface;
      a deployment mechanism; and
      a deployable keel oriented longitudinally along the rod;
   inserting the intramedullary nail into an intramedullary canal with the keel in a retracted position; and
   actuating the deployment mechanism to non-rotatably deploy the deployable keel from a retracted position to a deployed position such that the deployable keel is received at least in part in the groove.

8. The method of claim 7, wherein the deployable keel comprises a tip, and wherein the tip is closer to the outer surface when in the retracted position as compared to the deployed position.

9. The method of claim 7, wherein the deployment mechanism is disposed at a proximal end of the rod and configured to actuate the transition of the deployable keel from the retracted position to the deployed position.

10. The method of claim 9, wherein the deployment mechanism comprises an actuator located in the proximal cap, and wherein the actuator is selected from the group consisting of a button, switch, knob, threaded nut, and lever.

11. The method of claim 9, wherein the rod further comprises: a lumen extending therethrough from a proximal end to a distal end; and at least one opening disposed along the rod and configured to receive at least a portion of the deployable keel.

12. The method of claim 11, wherein: at least a portion of the deployable keel is within the lumen when in the retracted position and outside of the lumen when in the deployed position; and the deployable keel is configured to pass through the opening when transitioning from the retracted position to the deployed position.

13. A method of installing an intramedullary nail comprising:
   providing an intramedullary nail comprising:
      a rod comprising a proximal portion and a distal portion and configured to transition from an expanded configuration to a compressed configuration;
      a compression mechanism configured to move the proximal and distal portions axially with respect to one another from the expanded configuration to the compressed configuration; and
      a radial expansion mechanism wherein the intramedullary nail is expandable or contractible in a radial direction resulting in a change in a volume of the intramedullary nail,
   inserting the intramedullary nail into a medullary canal;
   actuating at least one of the compression mechanism or the radial mechanism such that either the axial length or the radial width of the intramedullary nail changes.

14. The method of claim 13, the intramedullary nail further comprising an actuator assembly configured to actuate the compression mechanism and comprising an actuator located on the proximal portion of the rod, wherein the axial expansion is a mechanical expansion wherein the compression mechanism comprises a compression member configured for rotational movement.

15. The method of claim 14, wherein the compression mechanism and the actuator are each located in a proximal cap.

16. The method of claim 13, wherein the compression mechanism comprises an internally-threaded sleeve rotatably attached around the proximal portion of the rod and configured to mate with external threading on the distal portion of the rod.

17. The method of claim 16, wherein the internally-threaded sleeve is a gear member comprising a plurality of teeth extending around a periphery of the gear member.

18. The method of claim 13, wherein the compression mechanism comprises a compression member configured for linear movement.

19. The method of claim 13, wherein the compression mechanism comprises: a body portion configured to be received between the proximal portion and the distal portion of the rod; and a translation member configured to be received within the body portion and comprising a first angled surface configured to engage the proximal portion of the rod and a second angled surface configured to engage the distal portion of the rod.

20. The method of claim 13, wherein the compression mechanism is disposed between the proximal portion and the distal portion of the rod.

\* \* \* \* \*